United States Patent
Miller

(10) Patent No.: US 8,917,815 B2
(45) Date of Patent: Dec. 23, 2014

(54) ADJUSTABLE DYNAMIC FILTER

(76) Inventor: Zachary A. Miller, San Francisco, CA (US)

(*) Notice: Subject to any disclaimer, the term of this patent is extended or adjusted under 35 U.S.C. 154(b) by 311 days.

(21) Appl. No.: 13/609,362

(22) Filed: Sep. 11, 2012

(65) Prior Publication Data

US 2013/0003937 A1  Jan. 3, 2013

Related U.S. Application Data

(63) Continuation-in-part of application No. 12/819,267, filed on Jun. 21, 2010, now Pat. No. 8,287,187.

(51) Int. Cl.
  G21K 1/04 (2006.01)
  A61B 6/00 (2006.01)

(52) U.S. Cl.
  CPC ............... *A61B 6/547* (2013.01); *A61B 6/4291* (2013.01); *A61B 6/4452* (2013.01); *A61B 6/4405* (2013.01); *A61B 6/487* (2013.01); *A61B 6/502* (2013.01); *A61B 6/505* (2013.01)
  USPC .......................................... 378/150; 378/155

(58) Field of Classification Search
  USPC .................................. 378/145–155
  See application file for complete search history.

(56) References Cited

U.S. PATENT DOCUMENTS

| | | |
|---|---|---|
| 4,532,646 A | 7/1985 | Gilbert |
| 5,008,920 A | 4/1991 | Gralak |
| 5,241,578 A | 8/1993 | MacMahon |
| 5,388,143 A | 2/1995 | MacMahon |
| 5,772,574 A | 6/1998 | Nanko |
| 5,781,610 A | 7/1998 | Miles |
| 6,050,724 A | 4/2000 | Schmitz et al. |
| 6,438,211 B1 | 8/2002 | Weekamp et al. |
| 6,702,459 B2 | 3/2004 | Barnes et al. |
| 6,765,550 B2 | 7/2004 | Janick et al. |
| 7,147,371 B2 | 12/2006 | Hecker |
| 7,344,304 B2 | 3/2008 | Hardesty |
| 7,581,884 B1 | 9/2009 | Barnes et al. |
| 2002/0080922 A1 | 6/2002 | Kwasnick et al. |
| 2002/0150215 A1 | 10/2002 | Barnes et al. |
| 2002/0168052 A1 | 11/2002 | Castleberry |
| 2003/0026386 A1 | 2/2003 | Tang et al. |
| 2004/0028181 A1 | 2/2004 | Charles, Jr. et al. |
| 2004/0208394 A1 | 10/2004 | Kurata |
| 2006/0023832 A1 | 2/2006 | Edic et al. |
| 2006/0256917 A1 | 11/2006 | Jacobs et al. |

(Continued)

OTHER PUBLICATIONS

PCT Search Report, Oct. 5, 2011, pp. 1-8, International Searching Authority, US.

(Continued)

*Primary Examiner* — Hoon Song
(74) *Attorney, Agent, or Firm* — Keith D. Nowak; Libby Babu Varghese Carter & Ledyard & Milburn LLP

(57) ABSTRACT

A grid employs dynamic and adjustable grid lines that communicates with a transmitting object and/or a receiving object. The grid lines may be but not limited to liner, cross-hatched or pinwheel shaped. The grid may switch between opaque and translucent and the grid lines may target, calibrate to and track an object either transmitting or receiving. The grid may be employed as a filter or a privacy screen on a computer screen for instance. The grid lines are angled to match an angle of a user's position with respect to the grid.

15 Claims, 14 Drawing Sheets

(56) References Cited

U.S. PATENT DOCUMENTS

| | | |
|---|---|---|
| 2007/0104321 A1* | 5/2007 | Spahn .......................... 378/154 |
| 2008/0130837 A1 | 6/2008 | Heath et al. |
| 2008/0240357 A1 | 10/2008 | Jabri et al. |
| 2011/0051902 A1 | 3/2011 | Liu |
| 2011/0311032 A1 | 12/2011 | Miller |
| 2012/0033304 A1 | 2/2012 | Kim |
| 2012/0163534 A1 | 6/2012 | Nambu |
| 2013/0181896 A1* | 7/2013 | Gruhlke et al. ............... 345/156 |

OTHER PUBLICATIONS

Baig, Edward C. "em Power electronic eyeglasses let you change your prescription in a blink", Jan. 7, 2011, pp. 1-2, USA Today URL://content/usatoday.com/communities/technologylive/post/2011/01.

Lee, Johnny Chung, "Hacking the Nintendo Wii Remote", Pervasive Computing, Jul.-Sep. 2008, pp. 39-45, IEEE CS, US.

PCT Search Report, Written Opinion of The International Searching Authority, Feb. 20, 2014.

\* cited by examiner

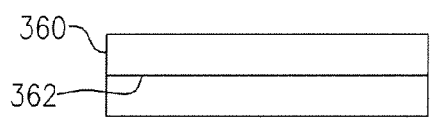
FIG. 8A  FIG. 8B
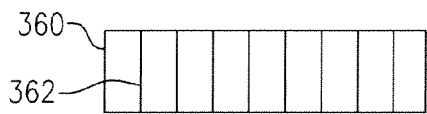
FIG. 8C  FIG. 8D

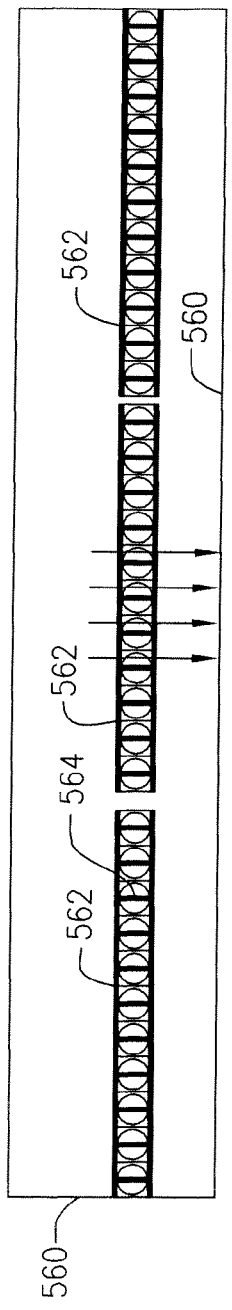
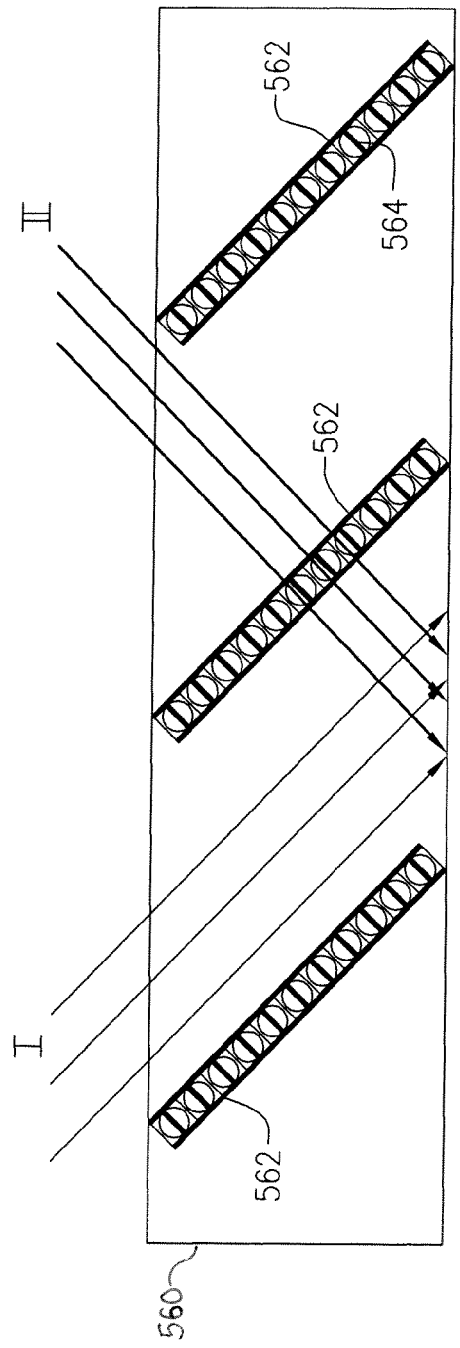
FIG. 10A
FIG. 10B

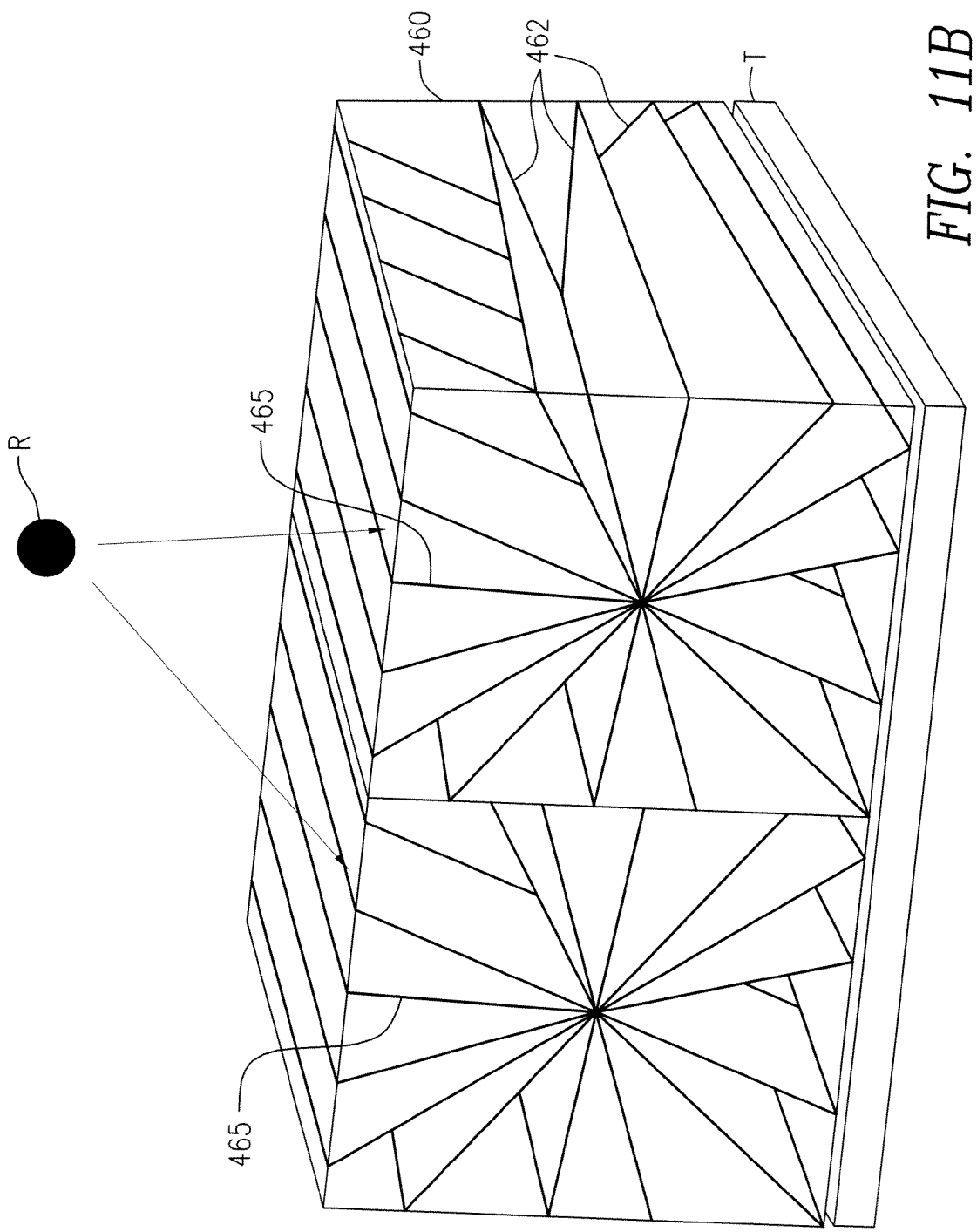

ADJUSTABLE DYNAMIC FILTER

PRIORITY AND RELATED APPLICATIONS

The present invention is a continuation-in-part of U.S. patent application Ser. No. 12/819,267, filed Jun. 21, 2010, entitled "Adjustable Dynamic X-Ray Filter," which is hereby incorporated by reference as if set fully herein. A PCT application, Ser. No. PCT/US2011/40622 entitled "Adjustable Dynamic X-Ray Filter" was filed on Jun. 16, 2011 and claims the benefit of Ser. No. 12/819,267.

FIELD OF THE INVENTION

The present invention relates to adjustable filters, in particular, to dynamically adjustable filters and privacy systems.

BACKGROUND OF THE INVENTION

In a hospital setting, mobile radiographic exams are performed on patients that are incapable of being moved, or are difficult to move. In tertiary care medical centers, mobile radiographic exams represent a significant percentage of the radiographic exams performed. X-rays passing through an object, such as a human body, experience some degree of scatter. The primary x-rays transmitted through an object travel on a straight line path from the x-ray source (also referred to herein as the x-ray focal spot) to the image receptor and carry object density information. Scattered x-rays form a diffuse image that degrades primary x-ray image contrast. In some patients, scattered x-ray intensity exceeds the intensity of primary x-rays. Scattering phenomena is well known and routinely compensated for in general radiography, fluoroscopy and mammography through the use of anti-scatter grids.

An anti-scatter grid is generally formed from alternating strips of x-ray opaque (or radiopaque) material and x-ray transmissive (or radiolucent) material. Lead may be used as the x-ray opaque material and plastics, aluminum or fiber may be used as the x-ray transmissive material. The grid is positioned between the object of interest and the x-ray image receptor plate and oriented such that the image forming primary x-rays are incident only with the edges of the x-ray opaque material. Thus, the majority of primary x-rays pass through the radiolucent spacer strips. In contrast, scattered x-rays are emitted in all directions after interaction with the target object and as such, scattered x-rays are incident on a larger area of the lead strips and only a small percentage of scattered x-rays are transmitted by the grid, as compared to primary x-rays.

The degree of scatter control for a given grid depends upon the grid ratio, which is defined as the ratio of the radiopaque strip thickness in the direction of the x-ray path to the width of the radiolucent spacer material as measured orthogonal to the x-ray beam path. Thus, the higher the grid ratio, the greater the scatter control. A high grid ratio, while more effective, is also more difficult to align relative to a focal spot. In order to compensate for x-ray beam divergence in a focused grid, the radiopaque strips are tilted to a greater extent with increasing distance from the center of the grid. The planes of the grid vanes all converge along a line known as the focal line. The distance from the focal line to the surface of the grid is referred to as the focal length of the grid. The focal line coincides with the straight line path to the focal spot. Thus, when the focal spot is coincident with the focal line of the grid, the primary x-rays have minimal interaction with the radiopaque lead strips and maximal primary transmission is obtained. Misalignment of the focal line of the anti-scatter grid with the focal spot diminishes primary x-ray transmission while scattered x-ray transmission remains unchanged. Thus, optimal primary x-ray transmission requires alignment (positional and orientational) of the focal spot with the focal line of the anti-scatter grid.

In general radiography, fluoroscopy and mammography, the image receptor and x-ray tube are rigidly mounted and in a fixed position relative to one another, thereby making focal spot and grid alignment a simple process. In mobile radiography, an image receptor is placed under a bedridden patient and the x-ray source is positioned above the patient. Since the relative separation of the focal spot and the image receptor is variable, determining the proper position and orientation of an anti-scatter grid between a patient and the image receptor becomes a difficult alignment problem. If a grid is not used, only a small fraction of the possible contrast is obtained in the x-ray image.

When grids are utilized in conjunction with mobile radiography, the grid is typically not aligned. Misalignment problems are diminished by utilizing a grid having a low ratio of 8:1 or less. Although x-ray image contrast is improved with the use of a low ratio grid, the contrast remains significantly lower than otherwise could be obtained with a properly aligned, high ratio grid having a grid ratio of 10:1 or greater.

Thus while mobile radiography is in many ways more convenient than fixed installation radiography, its clinical utility is diminished due to the inferior image quality caused by scattered radiation. This is a greater problem in mobile radiography due to the difficulty in producing the proper alignment of the focal spot with the anti-scattering grids. A means to produce proper alignment that is easy for the operator to use would significantly improve mobile radiographic image contrast and image quality, and thus increase the clinical utility of mobile radiography.

The mechanisms used with the grids for the x-ray arts provides a specific solution to a problem that may be more generalized and correlated to grids used in other areas for dynamic and adjustable filtration of waves including other components of the electromagnetic spectrum, fluids, and air. For instance, flexible and dynamic grids may be employed as privacy screens, filtering visual light in a manner that selectively follows a particular target. Here the grids used outside the x-ray arts will employ dynamically adjustable grid lines that target, calibrate to and track a user.

SUMMARY OF THE INVENTION

A system and method for determining the location of an x-ray source of an x-ray machine and for adjusting grid lines in an anti-scatter grid are disclosed. In one embodiment, the invention uses a source locator in conjunction with an infrared (IR) transmitter and IR receiver to locate the x-ray source and to align grid lines with an ideal x-ray beam path. By aligning the grid lines with the beam path, images with increased contrast and reduced noise can be produced.

The present invention provides a system for determining location of an x-ray source of an x-ray machine such as a portable x-ray machine. The system includes an x-ray source and a source locator. The x-ray source emits x-ray beams which have an idealized beam path. The source locator is associated with the x-ray source and has a means of communicating its position like but not limited to an IR transmitter/receiver. The IR transmitter/receiver of the source locator transmits location information defining the location of the x-ray source with the location information being generated by the source locator. The system may further comprise an x-ray grid also having a means of communicating its position like but not limited to an IR transmitter/receiver and x-ray grid lines that adjust to the position information determined by the communication between the two elements, in this case the source locator and x-ray grid component which approximates the ideal path of the emitted x-ray beams. The grid lines selectively permit the emitted x-ray beams to pass through said x-ray grid and align with the idealized path of the emitted x-ray beams. The grid lines adjust to the idealized beam path and selectively permit the emitted x-ray beams to pass through the x-ray grid in response to the IR emissions received by the IR receiver.

The present invention also provides a system for obtaining x-ray images with increased contrast and reduced noise. The system includes an x-ray beam source and an adjustable x-ray grid. The x-ray beam source emits x-ray beams and has a source locator associated therewith for determining the location of the x-ray source. The x-ray grid includes a plurality of grid lines comprising alternating radiopaque and radiolucent material. The grid lines of the x-ray grid may be adjusted to said x-ray beam source using an electromagnetic field, a servo motor or other computer driven mechanisms. The grid lines may be adjusted between a first unobstructed position that permits x-ray beam emissions to pass through the grid, and a second obstructed position that prohibits x-ray beam emissions from passing through the grid. The grid lines may comprise strips of material or individual radiolucent spheres with radiopaque material disposed in a central plane of each radiolucent sphere. The radiolucent material has a first charged side and a second charged side, where said first charged side is an opposite charge from said second charged side.

The present invention further provides a method of adjusting grid lines in an anti-scatter grid by providing an x-ray source, providing an adjustable x-ray grid and adjusting said x-ray grid lines to align with x-ray beam emissions of said x-ray source. In one embodiment radiolucent spheres include a layer of radiopaque material disposed in a central plane of each sphere. The adjustment means selectively align said x-ray grid lines to permit passage of said x-ray beam emissions through said x-ray grid. The adjustment means also includes use of a computer that receives location information obtained by the source locator to selectively align said x-ray grid lines to an idealized path of said x-ray beam emissions and to permit passage of said x-ray beam emissions through said x-ray grid.

The present invention also provides a device and method for filtering other elements including other parts of the electromagnetic spectrum including visible light as well as fluid and airflow. The filter is dynamic in that grid lines of the device adjust to a target based on information it receives from a source and/or the target or receiver.

The present invention provides a dynamic privacy screen having a display device or a grid that includes dynamic grid lines therein. The display device has a motion sensor such as but not limited to a IR LED emitters. The dynamic grid lines may have the capability to transition anywhere between an opaque state and a clear state and can be oriented to have an angle anywhere between 0 to 180 degrees. The grid lines are dynamic in that the lines adjust to an angle that matches an angle of a tracked object to the grid. A tracked object may include an individual user of a screen such as a computer screen, smartphone screen, tablet screen, or a television screen. The tracked object may have a marker that is sensed by the motion sensor of the display device or maybe tracked via use of integrated systems already employed on said device like but not limited to a forward facing video camera. The users will have the ability to calibrate the location of the grid with respect to the tracked object and the users field of vision in a similar manner to the x-ray grid example where the beam source itself can have a surrogate of its position encoded within the system. The detection of the marker by the sensor defines a location information about the tracked object and/or the display device. The location information is sent to a computer and is used to adjust the angular orientation of the grid lines to match the angle of the tracked object to the display device. Similarly, the video camera can employ existing software including but not limited to facial recognition software. When the grid lines are opaque and the location information is obtained, the computer will adjust the grid lines to be in line with the tracked object. With this alignment the tracked object or computer user, for instance, will be able to perceive transparent areas on the display device. An object not in line with the opaque grid lines will not perceive transparent areas on the display device but rather will see only the opaque areas on the display device. For instance an unmarked user standing next to the tracked object will only see the opaque lines and thus an opaque display screen.

BRIEF DESCRIPTION OF THE DRAWINGS

FIG. 7 shows a top view of the grid shown in FIG. 6 when the grid is turned on.

FIG. 8A show a grid line orientation at zero degree or one hundred eighty degrees.

FIG. 8B show a grid line orientation at about 45 degrees.

FIG. 8C show a grid line orientation at 90 degrees.

FIG. 8D show a grid line orientation at about 135 degrees.

FIG. 10A shows a grid of a third alternative embodiment with grid line oriented at about 0 degrees.

FIG. 10B shows the grid of FIG. 10A with grid line oriented at about 135 degrees.

FIG. 11B shows two grids of FIG. 11A beside each other.

DETAILED DESCRIPTION OF THE INVENTION

Figure 1:
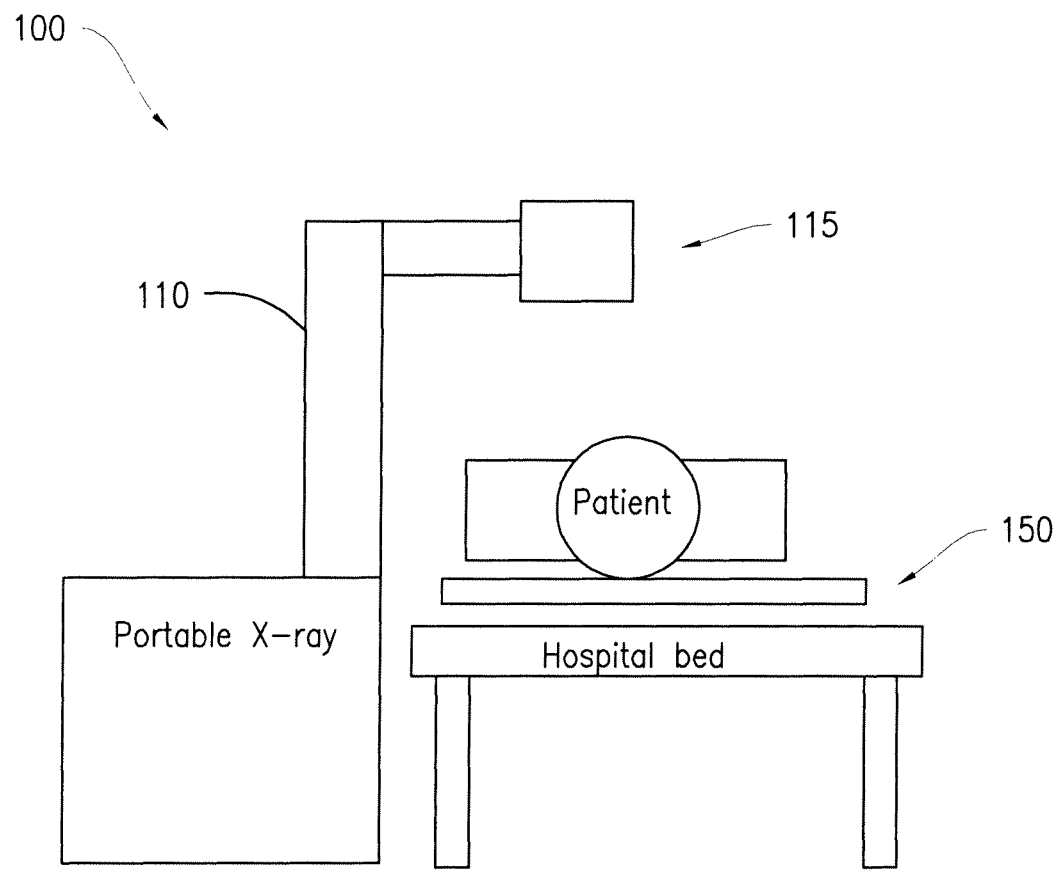
FIG. 1 is an illustration of a portable x-ray apparatus according to the present invention.
Figure 3:
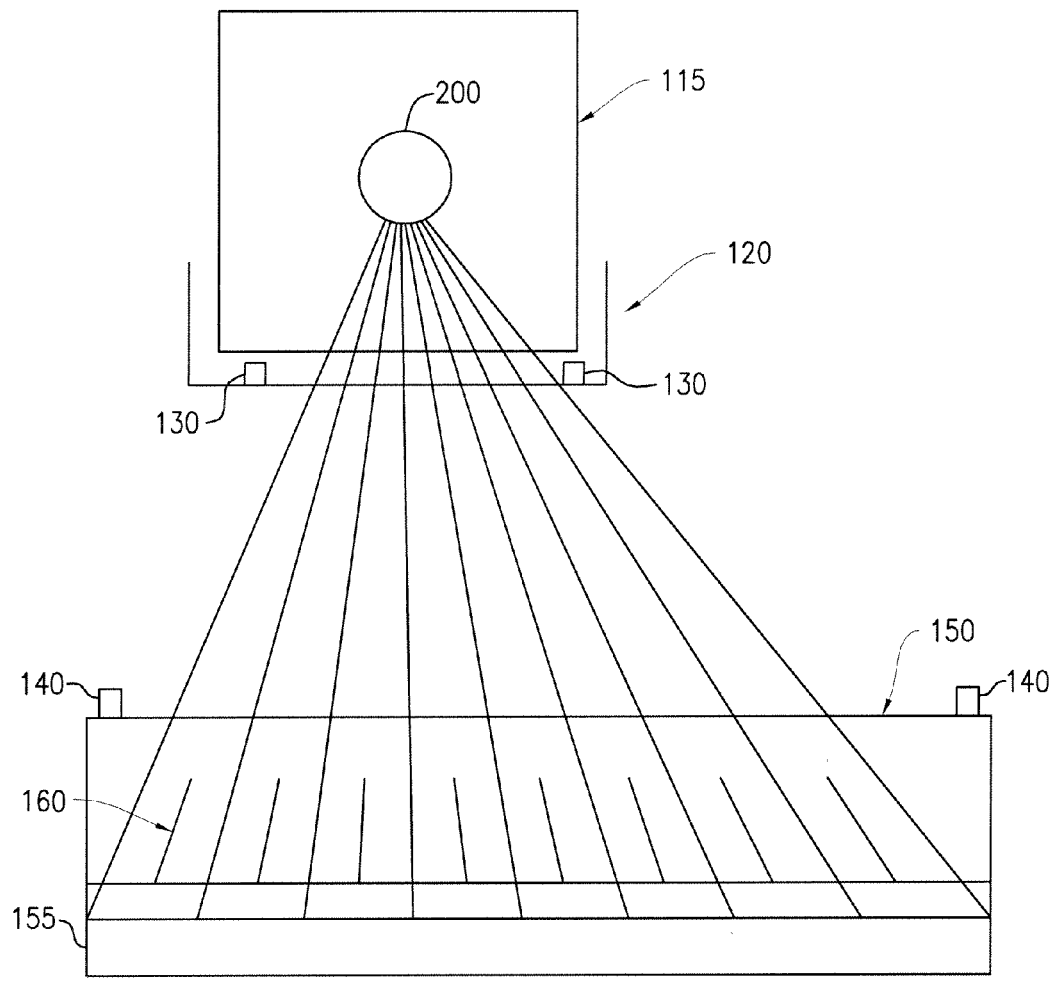
FIG. 3 is an embodiment of an x-ray plate employed in FIG. 1.

FIGS. 1 and 3 show a system 100 of the present invention for aligning x-ray emissions from an x-ray machine and for adjusting grid lines in an anti-scatter grid to obtain diagnostic image information with increased contrast and reduced noise due to scattered x-rays. The system 100 includes a portable x-ray machine 110 having an x-ray head 115 and an x-ray plate 150 used to removably receive an x-ray film cassette or digital x-ray detector 155. In one embodiment, a source locator 120 is attached to the housing of x-ray head 115 of x-ray machine 110 and x-ray plate 150 is attached to a flexible filter, anti-scatter grid 160. Both the source locator 120 and the flexible filter, anti-scatter grid 160 are mechanisms used to facilitate the acquisition of images with increased contrast and reduced noise when compared to images obtained using prior art portable x-ray machines and prior art grids.

Figure 2A:
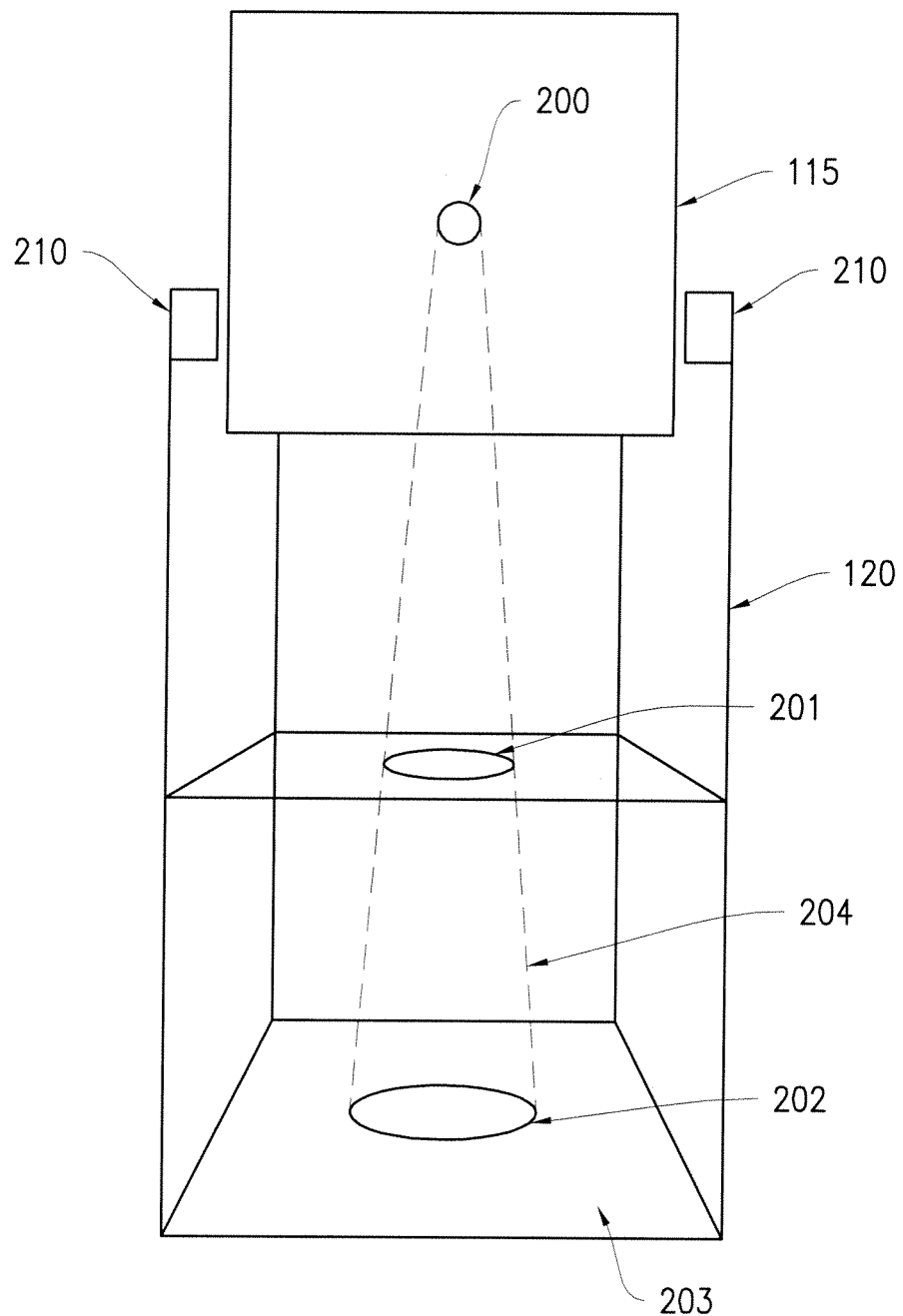
FIGS. 2A and 2D are illustrations of a source locator disposed on an x-ray source of the portable x-ray apparatus according to FIG. 1.

Referring now to FIG. 2A, there is shown a source locator 120 in greater detail. The purpose of source locator 120 is to determine the location of the x-ray source 200, and to record that location information in an appropriate digital storage device. The digital storage device is then associated with circuitry affixed to x-ray head 115 so that once the source locator is removed, or the x-ray head itself is moved, the location of the x-ray source in a particular x-ray head is stored and accurately known at all times.

Shown in FIG. 2A is x-ray source 200, the location of which must be determined, x-ray opaque object 201 and an image 202 of the x-ray opaque recorded on film 203. As described below, determination of the size differences between object 201 and image 202, along with appropriate computer calculations based on these differences, allow a precise determination of the x-ray source location. When the mobile x-ray machine is turned on x-ray radiation 204 is generated which passes over object 201 and is recorded on film 203 as image 202. As object 201 is x-ray opaque, the size of image 202 will vary based on the relative locations of x-ray source 200, object 201 and image 202.

Figure 2B:
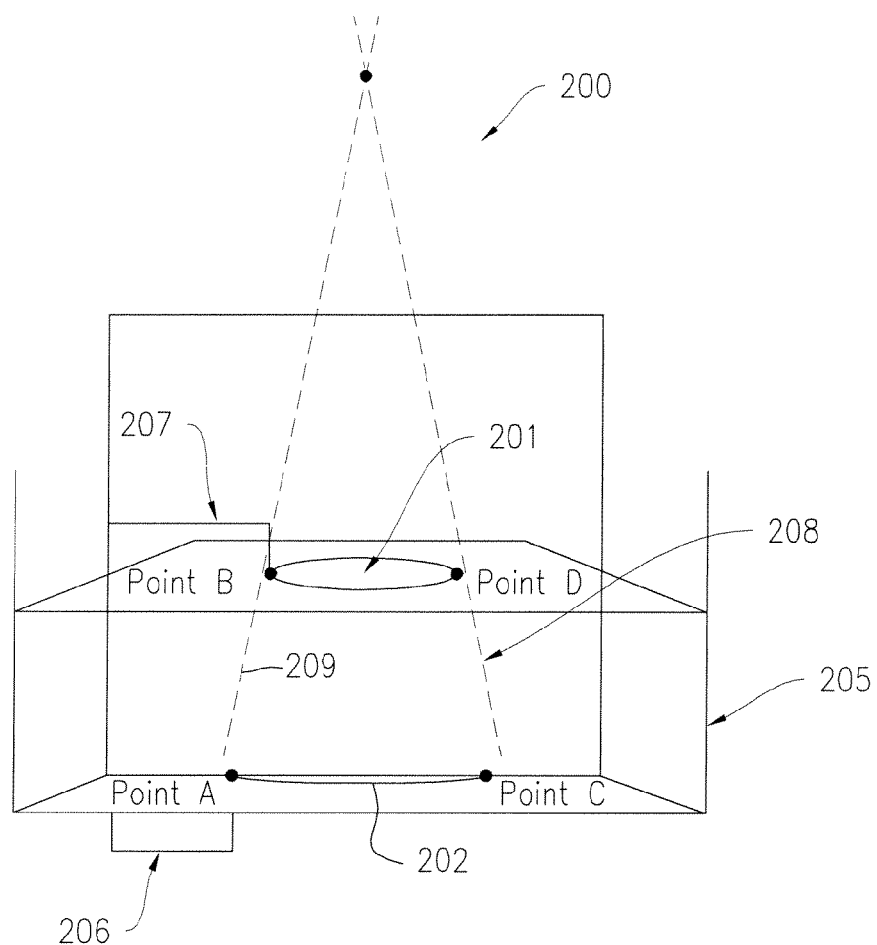
FIGS. 2B and 2C illustrate the manner in which the location of the x-ray source can be calculated.

Referring now to FIG. 2B, there is shown the manner in which the location of the x-ray source can be calculated. More particularly, the location coordinates of Points A and C are known as the "Y" dimension (distance 205) is known and fixed. Similarly distance 207 is known, so that the locations of Points B and D are known but distance 206 is variable and not known. Using known techniques, the difference in size between object 201 and image 202 can be readily determined.

Figure 2C:
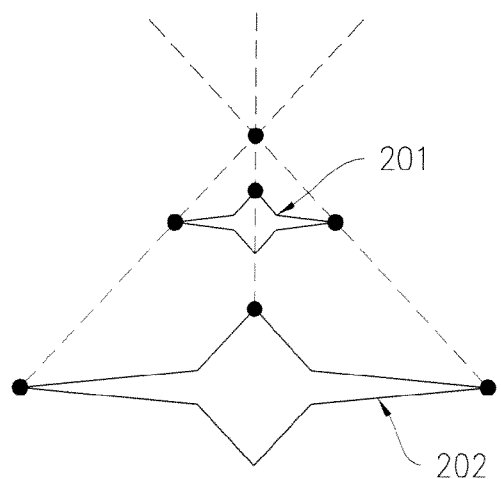

Knowing the location of Points D and C it is possible to calculate the relative angle of line 208 and knowing that angle it is possible to calculate the correct angle of line 209. The extension of lines 208 and 209 can be calculated to determine the precise location of x-ray source 200. It is to be understood that the known calculations described above would be accomplished on a computing device (not shown) associated with source locator 120. FIG. 2C illustrates the use of a star-shaped object 201, which represents an example of a figure with more distinct visual landmarks than the disc 201 shown in FIG. 2B, which may be employed to simplify the needed calculations.

Figure 2D:
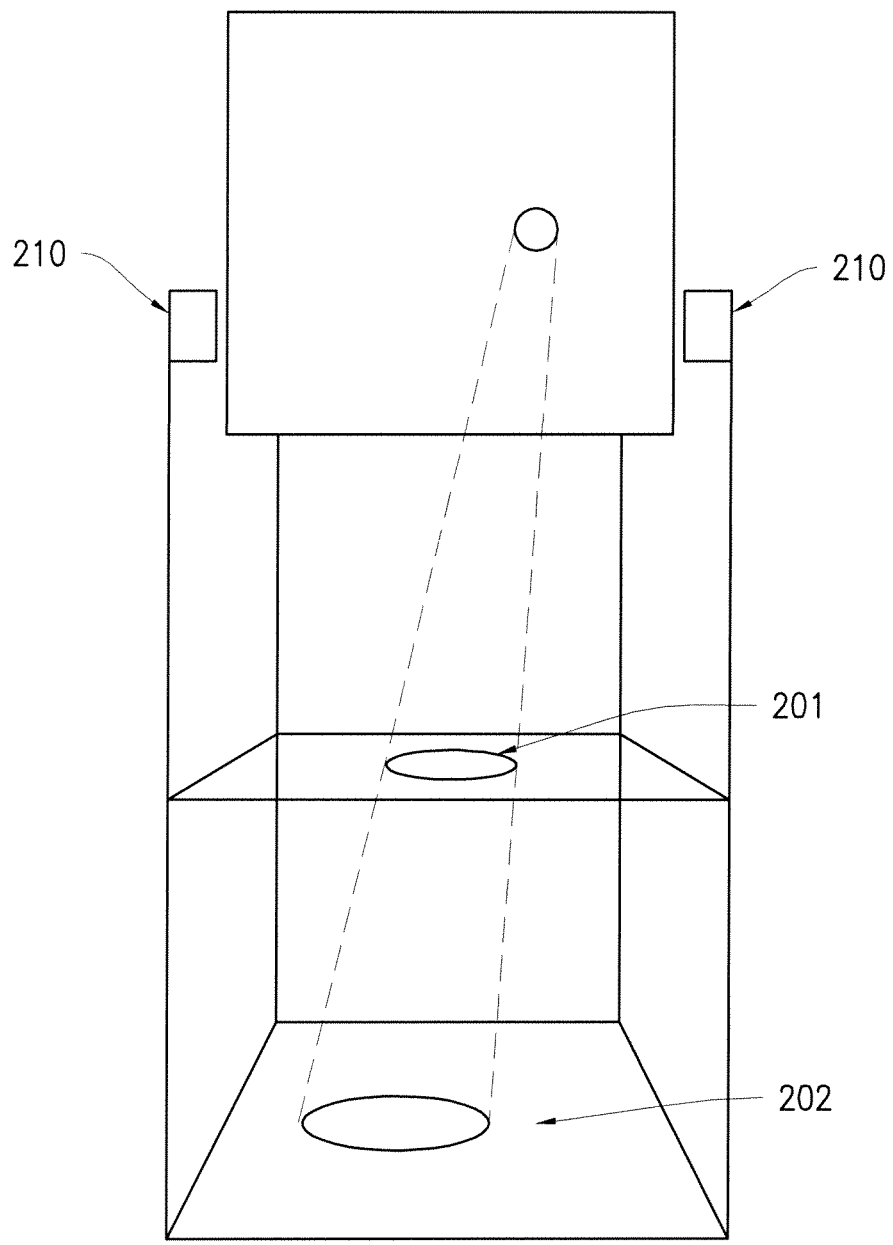

FIG. 2D shows an example where the x-ray is off center but the same process described above can be used to calculate its precise location. FIG. 2D also illustrates a representation of the digital storage device 210 described above in which the location information for x-ray source 200 is stored.

Referring specifically to FIG. 3, the source locator 120 is disposed on, integrated with or removably attachable to the x-ray head 115 of the x-ray machine 110. The locator 120 is used to determine the location of the actual x-ray focal spot 200 of the portable x-ray machine 110 as described above. The source locator 120 has, for example, infrared (IR) transmitters 130 disposed thereon and x-ray plate 150 has, for example an IR receiver 140 disposed thereon. The IR transmissions from transmitter 130 are received by IR receiver 140 in order to transmit the location of the x-ray source 200. It is understood that the location of the x-ray source 200 is stored in digital device 210, which stored information is used by IR transmitter 130. The general concept of using an IR transmitter and an IR receiver to transmit the location of a particular object is known. See for example U.S. Pat. No. 5,627,524. This system or similar known techniques can be used in accordance with the present invention.

After the location of x-ray source 200 has been determined and grid 160 adjusted as described below, source locator 120 can be removed from x-ray head 115. However the location of x-ray source 200 remains stored in digital storage device 210 so that the location of source 200 is available for subsequent use of the portable x-ray machine.

Figure 4:
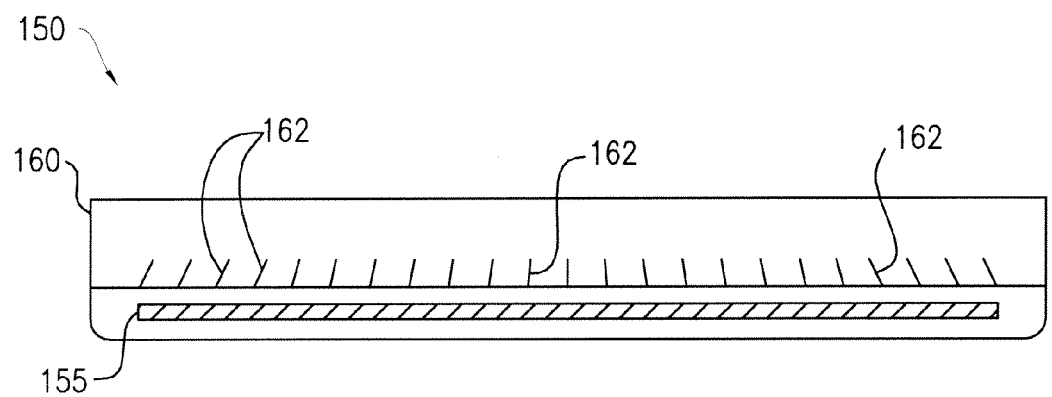
FIG. 4 is another embodiment of an x-ray plate employed in FIG. 1.

Referring now to FIG. 4, an embodiment of the x-ray plate 150 is shown. In one embodiment, the flexible filter, anti-scatter grid 160 is attached to the x-ray plate 150 that is used to removably receive detector 155. In other embodiments, the grid 160 may be removably attached to the x-ray plate 150. In use, the x-ray plate 150 would be oriented so that a patient would be situated on top of the grid 160 of the plate 150 with the detector 155 being disposed therebelow. The grid 160 reduces the effect of scattering by preventing scattered x-rays from reaching the detector 155.

The detector 155 may include an x-ray photosensitive film or a digital x-ray detector. For example, a suitable digital detector may include a cesium iodide phosphor (scintillator) on an amorphous silicon transistor-photodiode array having a pixel pitch of about 100 micrometers. Other suitable detectors may include a charge-coupled device (CCD) or a direct digital detector which converts x-rays directly to digital signals. While the photosensitive film is illustrated as being flat and defining a flat image plane, other configurations of the photosensitive film and digital detectors may be suitably employed, e.g., a curved-shaped photosensitive film or digital detector having a curved image plane.

Still referring to FIG. 4, the grid 160 has adjustable and dynamic grid lines 162 that are adjusted in response to the location of the x-ray focal spot as determined by source locator 112. This creates an idealized beam path of the x-ray emissions from the x-ray source 200. The grid 160 communicates with the source locator 120 via the IR transmitters and receivers described above in order to determine the idealized path of x-ray beams and then, based on the idealized path, the grid lines 162 adjust to line up with the idealized path. The grid lines 162 comprise a set of individual strips of radio-paque material and a set of individual strips of radiolucent material as described above.

In one embodiment, the radio-opaque material of the grid lines 162 comprise parallel lead louvers that employ servo motors to adjust the lead louvers based on the calculated idealized path. In this embodiment, a computer system may be used to obtain the idealized path information from the source locator, calculate the location of the focal spot and then adjust the louvers using the servo motor.

Figure 5A:
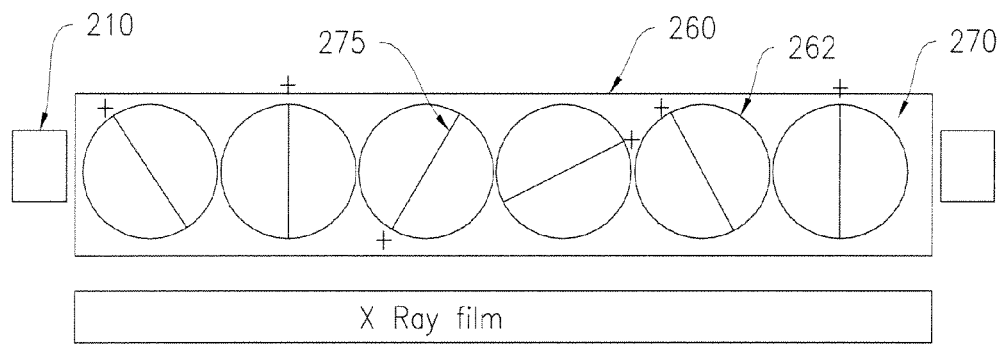
FIGS. 5A-5C illustrate the use of radiolucent spheres as embodiments of an x-ray grid.
Figure 5B:
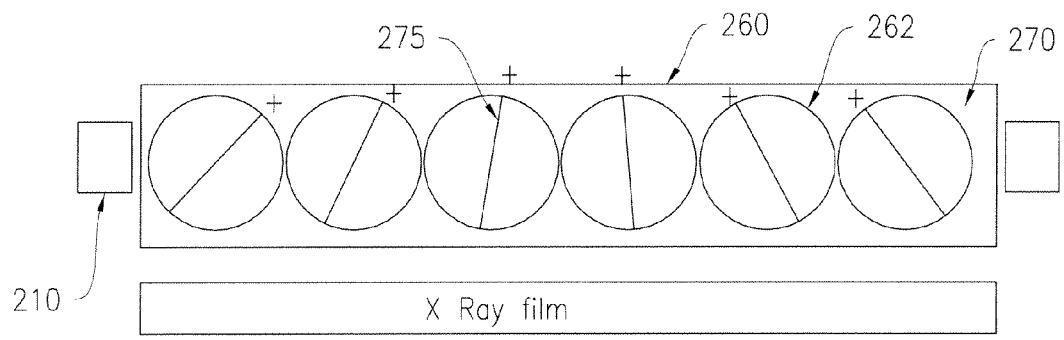
Figure 5C:
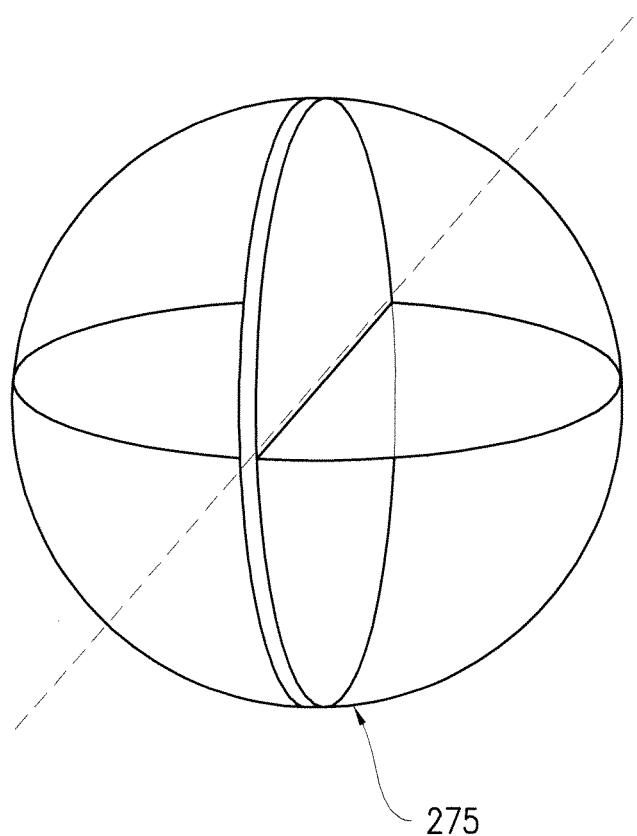

FIG. 5A shows another embodiment of x-ray plate 150 that comprises a grid 260 formed of grid lines taking the form of spheres 262 floating in a fluid matrix. The grid 260 would be part of a fluid system where the spheres 262 exist in one plane, or planar system. The spheres 262 may be suspended in any type of fluid or semi-fluid radiolucent material 270. Each sphere 262 has an arrangement of radio-opaque material 275 disposed therein, in this example the arrangement is in the shape of a plane. For instance, each sphere 262 has a thin layer of lead or similar radio-opaque material 275 that cuts through the sphere 262 in the center plane 275. Each sphere 262 would have the same polarity so that each center plane of each sphere 262 would align in response to the application of an appropriate electromagnetic field. When the idealized x-ray path is determined, as described above the control computer would apply an electromagnetic field to the planar system of the grid 260 so the lead plane 275 of the each sphere 262 aligns to the idealized path emitted from the x-ray source 200. By using an electromagnetic field, the spheres 262 are selectively adjusted to obstruct or permit x-ray beam emissions from the x-ray source 200. FIG. 5B illustrates one specific alignment of spheres 262 and FIG. 5C illustrates a sphere 262 having more than one plane, specifically two planes in this case, which may increase the performance of the anti-scatter grid.

The mechanics of the grid described above may be employed in fields outside of the x-ray technology arts. For instance, alternative grids may be employed to control or direct airflow, fluid movements, or other wavelengths within the electromagnetic spectrum for example light transmissions either from a transmitting object T or to a tracked receiving object R. In one embodiment the grid 360 is used with a transmitting object T which may be a screen of a computer or television and a tracked receiving object R which may be an individual or user of the computer or television. See FIG. 6

Figure 6:
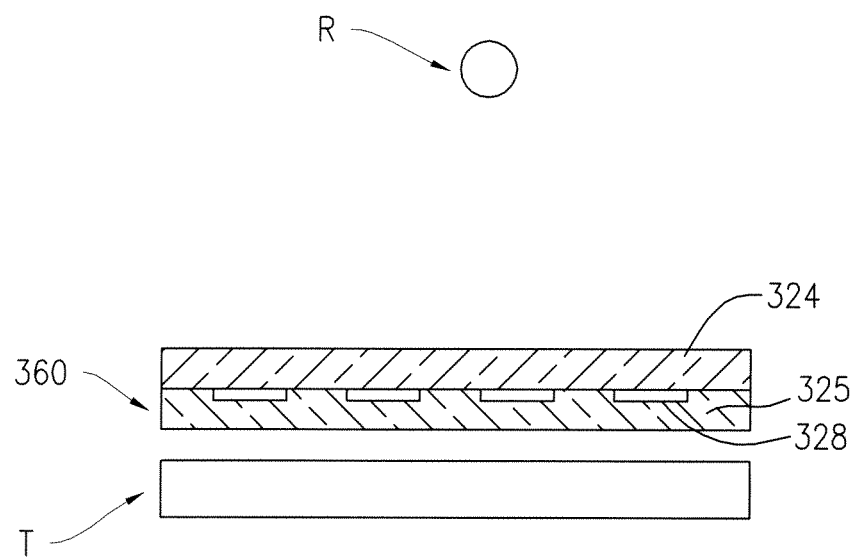
FIG. 6 illustrates a grid of an alternative embodiment.
Figure 7:
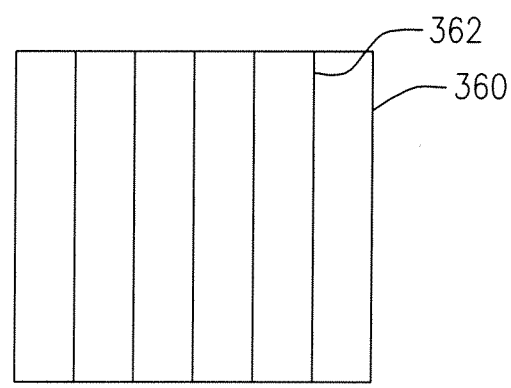

In one embodiment, grid 360 is a screen or display device that may employ LCD or LED technology to define adjustable and dynamic grid lines 362. In other embodiments, the grid 362 lines may comprise chemicals, IR LED or other technology. In another embodiment the chemical grid lines may comprise photochromatic technology. FIG. 6 describe the grid 360 which uses LCD or LED technology. Grid 360 may be composed of upper and lower transparent plates 324 and 325, respectively, which are sandwiched together. The transparent plates 324, 325 establish a light transmission path through grid 360. One of the plates, plate 325 in the exemplary display shown in the drawing, contains excisions or troughs exemplified at 328. The troughs 328 each contain a pool of liquid crystal material and are configured in any shape or configuration. In one embodiment, the configuration is of sets of parallel linear elements or of a crosshatch orientation. Conductive paths (not shown) extend to each of the liquid crystal pools in the respective troughs to afford excitation from a circuitry (not shown) cooperating with the grid 360 so as to display output adjustable and dynamic grid lines 362 on grid 360. See FIG. 7.

As is known, excitation of the elements in a liquid crystal display causes the excited element to become relatively opaque to light transmission. The output shown in FIG. 7 displays the adjustable and dynamic grid lines 362 as opaque regions in the form of the dark lines, the remaining portions of the grid 360 is transparent. The opaque regions can be selectively excited or turned on and off. When the elements are excited or turned on, the grid lines 362 are opaque. When the elements are not excited or turned off, the grid lines 362 are clear. The grid lines 362 are capable of achieving an angular orientation between 0 to 180 degrees. See FIGS. 8A-8D.

It should be noted that the plates 324, 325 and the troughs 328 may be made to have any dimension thereby permitting the excited elements, grid lines 362 when opaque, to have any dimension such as width and height. In a related theme, where the grid lines 362 have any dimension said grid 360 and said adjustable and dynamic grid lines 362 may be used as a privacy screen. The grid 360 may be placed over and be parallel with a transmitting object T such as a computer screen to filter light transmissions from the transmitting object T, a computer screen, to an intended receiving object R, a computer user. In an alternative embodiment, the grid 360 mayZ be integrated with the transmitting object T.

As mentioned above, when the grid lines 362 are turned on they are opaque but when the elements are turned off the grid lines 362 are transparent. When the grid 360 is transparent the angle of the grid lines 362 is immaterial. However, when the grid lines 362 are opaque the angle of the grid lines 362 can be used to filter or direct light from the transmitting object T, the computer screen, to the receiving object R, the user. See FIGS. 8A to 8B. In one embodiment, the grid lines 362 may mimic venetian blinds in that the grid lines 362 divide the grid 360 into strips that may be adjusted or placed at an angle with respect to an angle at which a transmitting object T and/or the receiving object R is to the grid 360. For instance, looking at FIGS. 8A-8D, the grid lines 362 at zero degrees (or 180 degrees) do not let any light through. Thus no light would pass through the grid 360 regardless of whether the receiving object R was placed at any three reference points identified by points A, B and C. See FIG. 8A. Grid lines 362 turned at about a 45 degree angle (see FIG. 8B) can be seen by reference point C, those at a 90 degree angle can be seen by reference point B (see FIG. 8C) and those at about 135 degree angle can only be seen by reference point A (see FIG. 8D.)

Figure 9:
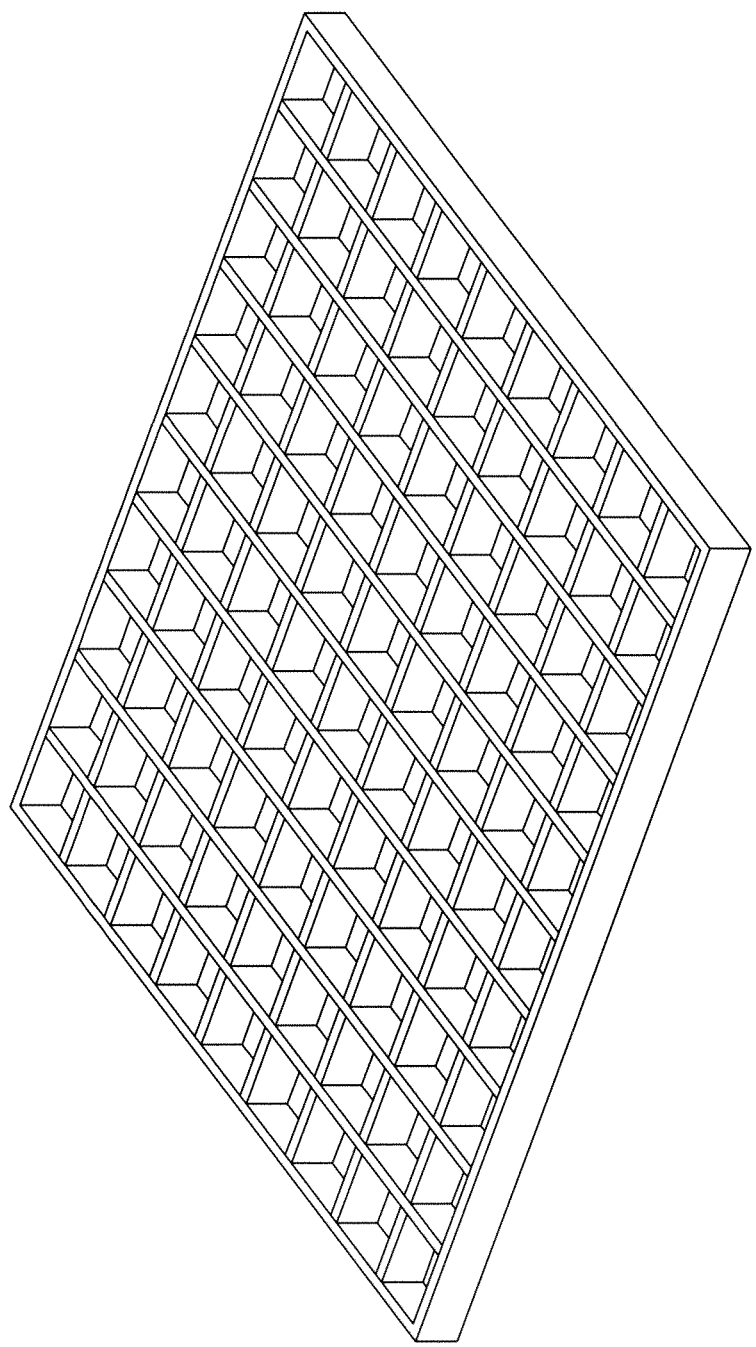
FIG. 9 shows a grid of a second alternative embodiment.

In another embodiment, the grid lines may have a crosshatch orientation. The crosshatch grid lines may not have a transparent state and will be opaque. If the grid 360 having the crosshatch grid lines were oriented in the same position as that shown in FIG. 6, that is between the transmitting object T and the receiving object R, then in a resting state or when the crosshatch grid lines are perpendicular to the transmitting object T, the receiving object R can look through the crosshatch grid lines and see the transmitting object T. However, when the crosshatch grid lines are not be perpendicular or askew to the transmitting object T, the receiving object R may only view the transmitting object T through the grid 369 when the receiving object R is in line with the crosshatch grid lines. If the crosshatch grid lines are designed to track the receiving object R then the crosshatch grid lines will be in line with the intended receiving object R. See FIG. 9.

As a further extension of the grid 360, grid 560 is shown where each grid line 562 is itself may be made up of smaller grid lines 564. See FIG. 10A. The grid 560 thus has the ability to selectively let light through each grid lines 562 and 564 at a different angles. See FIG. 10B. Where rays I pass through grid lines 562 and rays II pass through grid lines 564. Here two receiving objects R can be targeted to view the grid 360. For instance, the two receiving objects R can be a left and right eye of a user R with each eye receiving rays either rays I or rays II. One eye can be targeted to be parallel to grid lines 562 and the other eye parallel to grid lines 564 thereby permitting 3D viewing of the transmitting object T.

In another embodiment, the grid could consist of a similar make up to that in FIG. 5A. In this case the spheres would be made up of a material translucent to light and material inside the sphere arranged in a multitude of arrangements. In one illustrative example, the perpendicular paths bisecting the sphere in 2 planes, would be opaque or have the ability to be selectively opaque (that is turn on or off).

In another embodiment the grid 460 may be composed of adjustable and dynamic grid array lines 462 that can take any multitude of shapes or designs. See FIG. 11A. The array lines 462 spread out like a fan or a water wheel. The array lines 462 may employ LCD, LED, IR LED, chemical or other technology such that elements can be selectively excited to be relatively opaque to light transmission. Each individual array line 462 may be made clear or opaque depending on element excitement.

The array lines 462 of grid 460 is arranged in varying angles between both the transmitting object T, the computer screen, and the receiving object R, the computer user. Here too when all array lines 462 are turned on, the grid 460 is opaque obscuring light transmissions from the transmitting object T, the computer screen. When all array lines 462 are turned off, the grid 460 is clear allowing the receiving object R, the computer user, to view light transmissions from the transmitting object T, the computer screen.

Figure 11A:
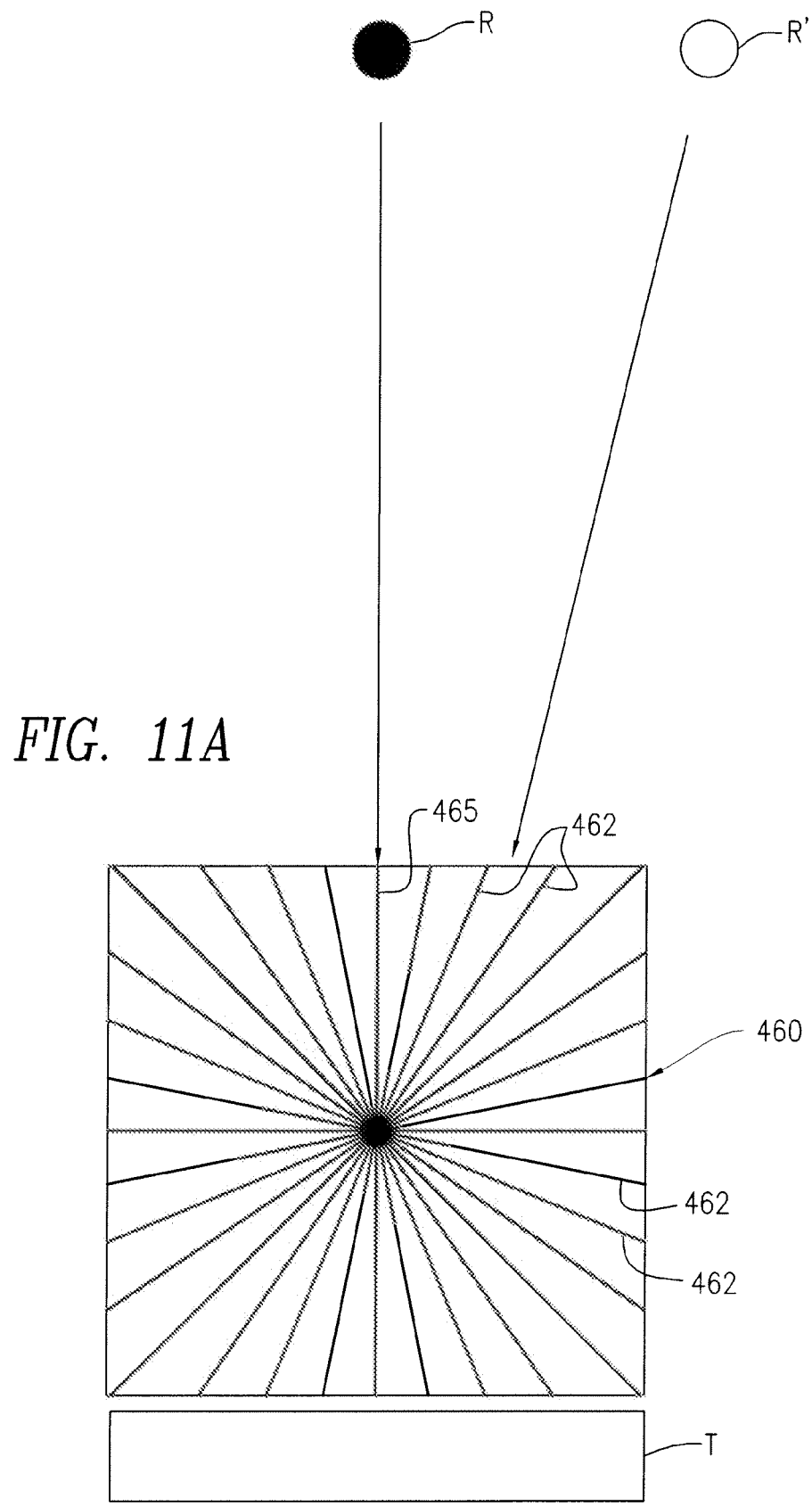
FIG. 11A shows a grid of a fourth alternative embodiment with grid lines oriented in an array.

When one or more array lines 462 are turned off, portions of the grid 460 are clear. For instance, array line 465 shown in FIG. 11A is parallel to the line of vision of the receiving object R and therefore when array line 465 is clear (or turned off) light transmissions can pass from the transmitting object T to the receiving object R. Thus when the receiving object R is the user and the transmitting object T is a computer screen, light transmissions from the computer screen T can be seen only by the user R. If the position of the user R changed to R' and thus was not in alignment with the array line 465 that is turned off, the R' user would not be able to see the light transmissions from the computer screen T. The R's user's line of sight would be focused on an adjacent or another array line 462 that is turned on and is opaque. The grid 460 may permit 3D viewing by employing a grid 460 for each eye. See FIG. 11B. Here each eye would be individually targeted to each grid 460. In a further embodiment the grids 460 may effectively be stacked one on top of the other.

The methods and mechanics of locating used in the grids 360, 460 of the alternative embodiments may mirror the IR mechanisms employed with the x-ray grids 160, 260 as well as other types of mechanisms like video camera motion tracking. In one embodiment, the user R may communicate with the grid 360, 460 by using IR communications. Here the user R would have a first communication or IR device such as a transmitting device or a marker and the grid 360, 460 would have a second communication or IR device such as a receiving device or motion sensor. Of course the first and second IR devices could be reversed for use with the grid 360, 460 and user R, respectively. If the user employs an IR device such devices may include IR devices placed on glasses, contact lenses, earrings, hats, bindi, or other devices worn on or by the user R.

In another embodiment, the mechanics of locating may employ video camera facial/object recognition software where the receiving party R may or may not be required to wear a marker, sensor or some sort of IR device. In this case the camera would be positioned on or within the device to be filtered and said video camera and computing software embedded within a computing system would track any number of targets adjusting the filter to the selected target. A computer (not shown) may be used to coordinate communication between said first and second locations whether they represent IR devices or video camera tracked entities. The computer will receive location information which is information obtained from the first and second locations, specifically from the motion sensor after having detected the marker of the tracked receiving object R. The technology for interaction between the transmitting object T and the receiving object R is better described in Johnny C. Lee, *Hacking the Nintendo Wii Remote,* 7 IEEE PERVASIVE COMPUTING, July-September. 39 (2008) and is incorporated by reference herein. The location information is used to adjust the angular orientation of the grid lines 362, 462 to match an angle of the receiving object R to the grid or display device 360, 460 when said grid lines are opaque. Thus, when the grid lines are opaque the receiving object R can perceive the grid lines as opaque and the areas without the grid lines 362, 462 (the rest of the grid 360, 460) as transparent. The angle of the tracked receiving object R to the grid 360, 460 dictates the angle of the dynamic grid lines 362, 462 within said grid 360, 460.

Once the act of locating is complete, the grid 360, 460 targets the user R, the grid 360, 460 can be calibrated to and track the user R. Calibration can occur in many ways. For instance, the user R may use left and right arrow keystrokes to adjust the grid lines 362, 462 of the grid 360, 460. In another embodiment, the user R can adjust the grid lines 362, 462 by touching a touch screen when the grid 360, 460 is employed with a touch screen. Yet another calibration technique mirrors the calibration technique described above with the x-ray source 200. As described above, location is determined on a size difference between an opaque object 201 and an image 202 of the object and computer calculations based on the difference. In another embodiment, the grid 360, 460, can use two different targets for calibration purposes. A first target is the user R and a second target is an object that can be manually placed between the IR device, video camera, or other system used to communicate location information to the grid 360, 460 and the user R. The second target may be anything that obstructs such as a television remote control or the users own hand. The user R places the hand or remote control between the user R and the grid 360, 460 and the grid lines 362, 462 adjust to the user R until the user R can adequately see through the grid lines 362, 462. Similar to the functioning in devices like the Nintendo Wii or Microsoft's Kinect, here an individual who is a distance away from a grid can turn on the privacy screen and then help adjust the targeting by hand gesture. The use of the second target between the first target and the transmitting object T permits the creation of an ideal path that the grid lines 362, 462 should adjust to.

In another embodiment, the grid lines of the grids 360, 460 may be adjusted using an electromagnetic field, a servo motor or other computer driven mechanisms, or might consist of the spheres floating in a fluid matrix 262 where the filter portion has the same capability to change its amount of transparency up to a level of becoming completely opaque. The grids 360, 460 may further be adjusted by use of a computer that receives location information obtained by the grids 360, 460 to selectively align said grid lines 362, 462 to an idealized path that permits light transmission, if desired, between a receiving object R and a transmitting object T.

Tracking occurs by having the grid 360, 460 or specifically the grid lines 362, 462 adjust to the movement of the users visual field. Tracking may also take place by using IR devices and techniques described in the targeting step. The present invention is different from the grids of the prior art. The prior art grids, such as privacy screens, do not adjust and only permit a clear view straight-on. In contrast, the grid 360, 460 of the present invention may be used by any receiving object R positioned at any angle from the transmitting object T.

While the present invention has been described in conjunction with specific embodiments, those of normal skill in the art will appreciate the modifications and variations can be made without departing from the scope and the spirit of the present invention. Such modifications and variations are envisioned to be within the scope of the appended claims.

The invention claimed is:

1. A dynamic privacy screen comprising:
   a display device, said display device having a motion sensor;
   dynamic grid lines, said grid lines are opaque in a first state and clear in a second state, said grid lines are disposed in said display device, said grid lines are capable of achieving an angular orientation between 0 to 180 degrees;
   a tracked object, said tracked object having a marker, said motion sensor detecting said marker of said tracked object and providing location information on said tracked object; and
   a computer, said computer receiving said location information, said location information adjusting the angular orientation of the grid lines to match an angle of the tracked object to the display device when said grid lines are in said first opaque state,
   wherein said angle of the tracked object to the display device dictates an angle of the dynamic grid lines within said display device.

2. The dynamic privacy screen of claim 1, wherein the grid lines are linear strips, wherein when said grid lines are in said opaque first state, the display device is separated into a series of said opaque grid lines alternating with a series of transparent areas.

3. The dynamic privacy screen of claim 1, wherein the grid lines are crosshatched, wherein when said grid lines are in said opaque first state, the display device is separated into a series of boxes of transparent areas.

4. The dynamic privacy screen of claim 1, wherein the grid lines are array shaped, wherein when said grid lines are in said opaque first state, the display device is opaque.

5. The dynamic privacy screen of claim 4, wherein one array in the array shaped grid lines is in said transparent second state, the display device in line with the one array is transparent.

6. The dynamic privacy screen of claim 1, wherein said grid lines comprise LCD, LED, chemical and photochromatic technologies.

7. The dynamic privacy screen of claim 1, wherein the marker and the motion sensor are corresponding IR devices.

8. The dynamic privacy screen of claim 7, wherein the marker is an IR LED and the motion sensor is an IR camera.

9. A method of adjusting dynamic grid lines in a grid comprising:
targeting a tracked object by a grid, said grid having dynamic grid lines and a first communication device, said dynamic grid lines are opaque in a first state and clear in a second state, said grid lines are disposed in said grid, said grid lines are capable of achieving an angular orientation between 0 to 180 degrees, said first communication device obtaining location information on said tracked object, said location information being processed by a computer to adjust angular orientation of the grid lines, when said grid lines are opaque, to match an angle of the tracked object to said grid;
adjusting the angular orientation of the grid lines to match the angle of the tracked object to said grid, said adjustment based on said location information; and
tracking said tracked object by said grid lines,
wherein said grid lines are in a clear second state the grid is transparent, and when the grid lines are in said opaque first state portions of the grid are opaque.

10. The method of claim 9, wherein said first communication device includes an IR camera, a sensor and a facial recognition software stored on a computer.

11. The method of claim 9, wherein said tracked object further includes a second communication device, said second communication device and said first communication device interact to produce said location information.

12. The method of claim 11, wherein said second communication device includes IR transmitters.

13. The method of claim 9, wherein said adjustment includes calculating a distance between said tracked object and a calibrating object, said calibrating object being positioned between said tracked object and said grid.

14. The method of claim 9, wherein said adjustment includes using keystrokes and touch screens.

15. The method of claim 9, wherein said tracking includes monitoring said tracked object using an IR camera, a sensor and a facial recognition software stored on a computer.

* * * * *